United States Patent [19]

Froesch et al.

[11] Patent Number: 5,106,832
[45] Date of Patent: Apr. 21, 1992

[54] METHOD FOR TREATING RENAL DISEASES

[75] Inventors: Ernst R. Froesch, Erlenbach; Hans-Peter Guler, Adliswil; Christoph Schmid; Jürgen Zapf, both of Zurich, all of Switzerland

[73] Assignee: Ciba-Geigy Corporation, Ardsley, N.Y.

[21] Appl. No.: 634,772

[22] Filed: Dec. 21, 1990

Related U.S. Application Data

[63] Continuation of Ser. No. 302,165, Jan. 25, 1989, abandoned.

[30] Foreign Application Priority Data

Feb. 5, 1988 [EP] European Pat. Off. ........ 88810071-6

[51] Int. Cl.⁵ .............................................. A61K 37/26
[52] U.S. Cl. ............................................. 514/3; 514/12
[58] Field of Search ....................................... 514/3, 12

[56] References Cited

FOREIGN PATENT DOCUMENTS 123228 10/1984 European Pat. Off. .

OTHER PUBLICATIONS

Hirschberg et al., Kidney International, vol. 32, Suppl. 22 (1987) pp. S21-S24.
Guler et al., New England J. of Med., vol. 317, No. 3 (1987) pp. 137-140.
Scheiwiller et al., Nature, vol. 323, Sep. 11, 1986, pp. 169-171.
Guler, in *Modern Concepts of Insulin-Like Growth Factors* (Spencer, ed., Elsevier 1991), pp. 583-590.
Guler et al., PNAS:U.S.A., 85:4889-4893 (1988).
Guler et al., *Acta Endocrinologica*, 121:101-106 (1989).
Hirschberg et al., *Kidney International*, 35:865-870 (1989).
Schoenle et al., Acta Endocrinologica, 108:167-174 (1985).
Zapf et al., *J. Clin. Invest.*, 68:1321-1330 (1981).
Guler et al., *PNAS:U.S.A.*, 86:2868-2872 (1989).

Primary Examiner—Howard E. Schain
Assistant Examiner—Choon Koh
Attorney, Agent, or Firm—Steven R. Lazar; Irving M. Fishman; JoAnn Villamizar

[57] ABSTRACT

Insulin-like growth factor I (IGF I) and pharmaceutical compositions comprising IGF I are useful in improving glomerular filtration and renal plasma flow and can be used for the treatment of patients suffering from renal diseases and for the preparation of therapeutic combinations for treatment of renal diseases.

6 Claims, 7 Drawing Sheets

METHOD FOR TREATING RENAL DISEASES

This application is a continuation, of application Ser. No. 302,165, filed Jan. 25, 1989, now abandoned.

FIELD OF THE INVENTION

The invention concerns a method for the treatment of patients for improving glomerular filtration and renal plasma flow by application of insulin-like growth factor I (IGF I) and pharmaceutical compositions comprising IGF I which are useful for this purpose.

BACKGROUND OF THE INVENTION

Renal diseases of acute and chronic nature are widespread in man. Examples of renal diseases are glomerulonephritis, interstitial nephritis, pyelonephritis, glomerulosclerosis, e.g. Kimmelstiel-Wilson in diabetic patients, and post-kidney transplant immune rejection. These diseases are caused by autoimmune processes, various drugs, bacterial invasion or degenerative lesions, respectively. The treatment of renal diseases depends on the causes, e.g. bacterial invasion is treated by application of antibiotics, or, another example, post-kidney-transplant immune rejection is treated by immunosuppression (glucocorticoids, cyclosporin A, etc.). Diminished glomerular filtration and renal plasma flow may be caused by all above mentioned mechanisms and as such could not be treated up to now. Whenever possible, treatment of above mentioned renal diseases consists in the elimination of the causes of the above mentioned pathogenic mechanisms. Consequences of the diminished glomerular filtration and renal plasma flow are the increased blood levels of nitrogene containing metabolites, such as creatinine, urea and uric acid, of pharmaca and their metabolites, as well as of kations and anions of mineral or organic salts. Some of these metabolites and ions are toxic and a surplus thereof may be the reason of certain diseases or at least unpleasant effects.

The major drawbacks of the present methods for the treatment of such toxic effects are that in the case of advanced renal disease they are mostly ineffective. So fare there are no drugs available that improve glomerular filtration and renal plasma flow. There is a definitive need to overcome these drawbacks.

Surprisingly IGF I was now found to improve glomerular filtration and renal plasma flow, in particular also over a prolonged period of time. Advantageously the salt and water balance of the whole body remains constant during treatment with IGF I. No salt or water retention, as seen with growth hormones was observed with IGF I.

IGF I has recently been shown to lower blood glucose in man after intravenous bolus injection (1). Other effects of IGF I are the growth-promoting actions which have been documented in several metabolic conditions which have low IGF I levels in common, e.g. hypophysectomized rats (2), diabetic rats (3) and Snell dwarf mice (4). Further, prolonged subcutaneous infusions of IGF I to hypophysectomized rats (5) led to a significant weight gain of the kidneys. Similar findings were reported in Snell dwarf mice (4). In all these studies there was no indication of any improvement of kidney function by IGF I. In particular there exists no report on the improvement of glomerular filtration and renal plasma flow during administration of IGF I.

OBJECT OF THE INVENTION

Object of the invention is to improve glomerular filtration and renal plasma flow thereby causing a lowering of the plasma levels of toxic metabolites, such as nitrogen containing compounds, e.g. creatinine, urea, uric acid of pharmaca and their metabolites, and of ions. Further object of the invention is to provide pharmaceutical compositions containing IGF I in dosage unit form and in such amounts as to achieve said beneficial effect.

DETAILED DESCRIPTION

Figure 1:
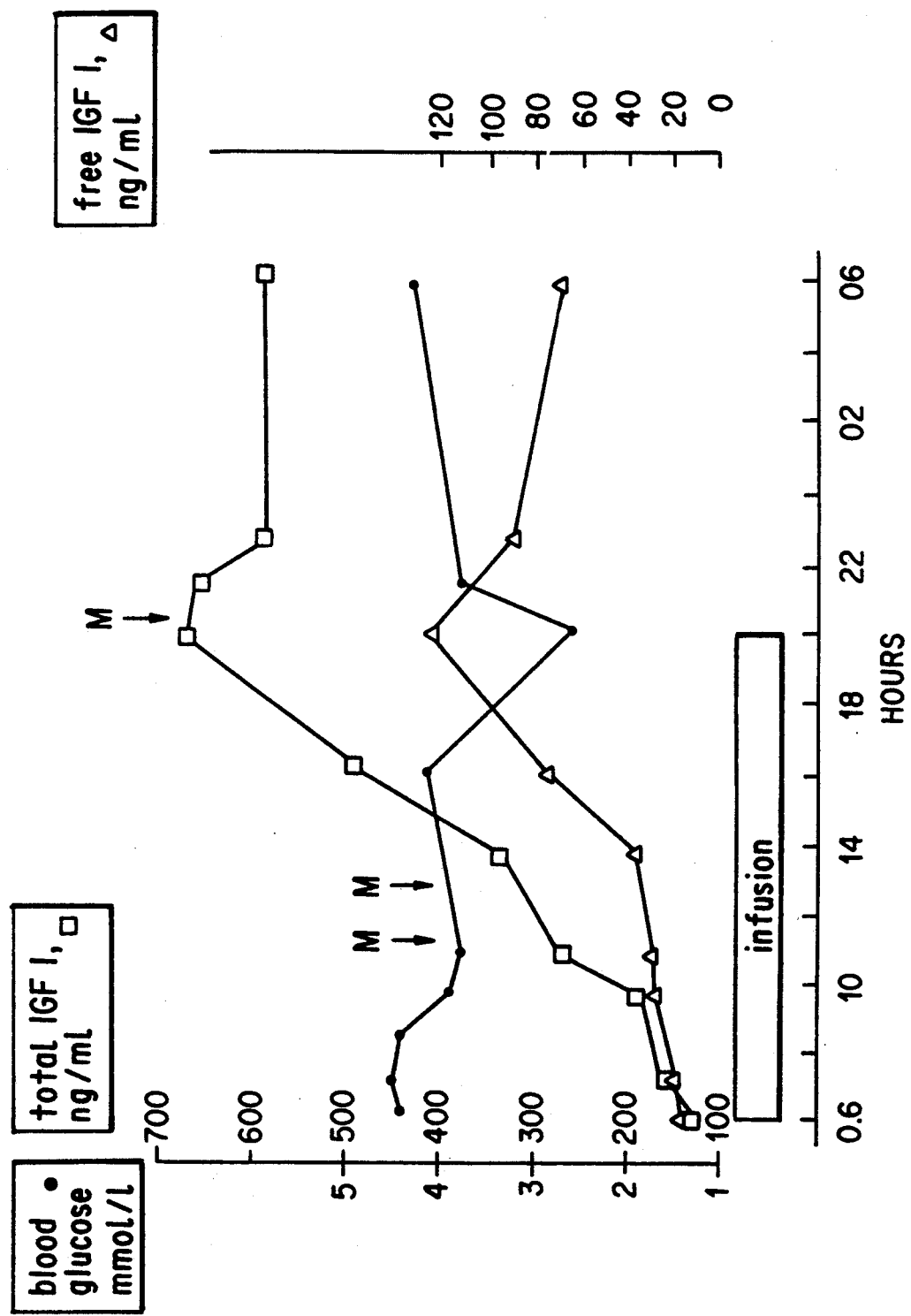

The invention concerns a method for improving glomerular filtration and renal plasma flow in patients suffering from impaired renal function, characterized in that an effective amount of IGF I is administered to such patients.

As improvement of glomerular filtration and renal plasma flow would be very desirable effects in patients suffering from renal diseases, the invention concerns also a method for the treatment of renal diseases, especially of glomerulonephritis, interstitial nephritis, pyelonephritis, glomerulosclerosis, e.g. Kimmelstiel-Wilson in diabetic patients, and kidney failure after kidney-transplantation, characterized in administering a therapeutically effective amount of IGF I that improves glomerular filtration and renal plasma flow.

The present method concerns in particular the treatment of man by using human IGF I, however, it can also be applied to animals having a diminished glomerular filtration and renal plasma flow.

Glomerular filtration is measured by determining the glomerular filtration rate which is defined as the creatinine or inulin clearance. Renal plasma flow is measured by determining the clearance of $^{125}$I-iodohippurate.

Any source of IGF I can be used whether from natural sources or synthetically produced. Preferred is recombinant human IGF I (rhIGF I), prepared e.g. according to EP 123 228.

An effective amount is defined as increasing the glomerular filtration rate and renal plasma flow, e.g. by about 30% and about 25%, respectively, above normal or subnormal.

In order to achieve this effect IGF I is administered intravenously, subcutaneously or intramuscularly in doses between about 24 $\mu$g/kg/day up to about 720 $\mu$g/kg/day, or if given continuously in doses of about 1 $\mu$g/kg/h up to about 30 $\mu$g/kg/h, either by two or three daily injections or by continuous subcutaneous infusions, e.g. via a minipump, respectively.

The dosage has of course to be adjusted to the degree of the renal insufficiency, the route of administration, the individual weight and general condition of the patient to be treated, and is finally dependent on the judgement of the physician. Caution should be taken that blood glucose is monitored and hypoglycemia prevented.

Pharmaceutical compositions for the treatment of renal diseases by improvement of glomerular filtration and renal plasma flow comprise an effective amount of IGF I, i.e. an amount of from about 10 mg to about 300 mg.

In general the pharmaceutical preparation contains an effective amount of the active ingredient together or in admixture with inorganic or organic, solid or liquid, pharmaceutically acceptable carriers which are suitable preferably for parenteral administration.

The active compound of the present invention is preferably used in the form of preparations or infusion solutions for parenteral, for example subcutaneous, intramuscular or intravenous, administration. Such solutions are preferably isotonic aqueous solutions or suspensions which can be prepared before use, for example from lyophilised preparations which contain the active ingredient alone or together with a pharmaceutically acceptable carrier. The pharmaceutical preparations may be sterilised and/or contain adjuncts, for example preservatives, stabilisers, wetting agents and/or emulsifiers, solubilisers, salts for regulating the osmotic pressure and/or buffers. The present pharmaceutical preparations, which may, if desired, contain further pharmacologically valuable substances, are produced in a manner known per se, for example by means of conventional dissolving or lyophilising processes, and contain from approximately 0.1% to 100%, especially from approximately 1% to approximately 20%, and in the case of lyophilisates up to 100%, of the active ingredient.

The invention concerns further the use of the pharmaceutical preparation for the treatment of a patient suffering from renal diseases that led to a deficient glomerular filtration and renal plasma flow.

The invention concerns also the use of IGF I for the manufacture of a pharmaceutical preparation for the treatment of renal diseases, such as caused by a deficient glomerular filtration and renal plasma flow, which may contain instructions for its use.

The invention concerns also a preparation or pack comprising IGF I, and which may include instructions for use.

Following is an example of a therapeutic combination according to the invention which, however, should not be construed as a limitation thereof. The term IGF I in the Examples, if not otherwise specified, refers to recombinant human IGF I (rhIGF I).

EXAMPLE FOR A PHARMACEUTICAL PREPARATION

Dry ampoules containing 50 mg or 300 mg of IGF I: ampoules of 8 ml or 50 ml, respectively, volume are filled with 5 ml or 30 ml, respectively, of sterile filtered 1% (w/v) aqueous solution of IGF I and lyophilized. The infusion solution is prepared by adding the respective volume (5 or 30 ml) of sterile water, physiological saline, or 0.1M acetic acid.

The therapeutic combination contains the desired number of ampoules necessary for one course of treatment, e.g. for 6 days, and optional instructions for application which stipulate the time during which the medicament should be infused.

1. Example for Treatment of Humans

Subjects

Two males (age/body weight/height: 1.: 38/65/172; 2.: 34/61/172) served as normal subjects in this clinical trial. Their body weight was ideal and they had no clinical evidence of illness and did not take any medication. Routine hematology, blood chemistry and endocrine parameters were within normal limits.

Experimental Protocol

During an initial control period baseline values were obtained after which IGF I was administered by continuous s.c. infusion during six days. This route of administration was selected in order to reach constant serum levels of IGF I. The study was concluded with a second control period. Food intake was strictly controlled during the whole study and consisted of 2500 kcal per day (25% protein, i.e. 1.9 g protein per kilogram body weight, 20% fat and 55% carbohydrate).

Subject 1: Both control periods lasted for three days. On the first day of treatment, IGF I was initially infused at an arbitrary dose of 32.0 µg per kilogram body weight and hour. This dose of IGF I caused hypoglycemia (see result section). 20.0 µg per kilogram body weight and hour during the next five days were found to be safe and blood glucose remained normal. The total amount of IGF I infused during six days was 184.3 mg.

Subject 2: Both control periods were five days. IGF I was infused at the same dose as in subject 1 (20.0 µg per kilogram body weight and hour) during a total of six days. The total amount of IGF I infused was 167.3 mg.

Infusion Device: A miniaturized insulin-infusion device (MRS 1 Infusor ®/Disetronic AG, Burgdorf, Switzerland) was used. IGF I was dissolved in 0.1M acetic acid. 25 µl per hour were infused. The infusor cartridge containing the IGF I was refilled after 3 days. A microcatheter was placed under the skin of the abdomen. It was changed after 3 days and placed at a location distant from the first one.

Venous Blood was obtained every morning between 6 and 7 a.m. It was immediately placed on ice and centrifuged one hour later. Serum or plasma was stored in 1 ml portions at −20° C. All assays were done in samples that had not been thawed before.

24 Hours-Urine collections were obtained throughout the study (6 a.m. to 6 a.m.). Several aliquots were stored at −20° C.

Recombinant Human IGF I (rhIGF I) used in the Examples has been prepared according to EP 123 228, has been characterized chemically and biologically and found to be identical to highly purified extracted human IGF I. The same material had been used in a previous study in man (1).

Assays

Total IGF I and free IGF I were measured by radioimmunoassay as described earlier (6). Blood glucose was determined by YSI 23A glucose analyzer. All other analyses were kindly performed in the Department of Clinical Chemistry of the University Hospital of Zürich.

Results

Dose finding in subject 1 (FIG. 1)

After three control days (without any hormone) the IGF I infusion was started at 6.30 a.m. at a rate of 32.0 µg per kilogram body weight and hour. Blood glucose was 4.4 mmol per liter, the serum level of total IGF I 120 ng per milliliter and that of free IGF I 20 ng per milliliter. 13.5 hours later, after the infusion of a total of 28.1 mg of IGF I and 8 hours after the last meal, blood glucose had fallen to 2.6 mmol per liter without any clinical signs of hypoglycemia. By that time the serum level of total IGF I had reached 683 ng per milliliter, and the serum level of free IGF I was 123 ng per milliliter. The infusion was stopped overnight and started again on the next morning at 6.30 a.m. at a rate of 20.0 µg per kilogram body weight and hour. This dose was kept constant during the subsequent 5 days in subject 1 and was also used during the whole six day infusion period in subject 2.

Clinical Observations

Apart from the hypoglycemic episode in subject 1 on the first day of the IGF I infusion, no other such event was recorded. Both subjects felt normal throughout the study. Blood pressure, pulse rate, body temperature and body weight remained stable.

Blood Glucose

Blood glucose was monitored daily after overnight fasting (at least 12 hours) and remained within normal limits throughout the study. In subject 2 blood glucose levels measured every hour during one night of IGF I infusion were between 3.6 and 4.4 mmol per liter.

Figure 2A:
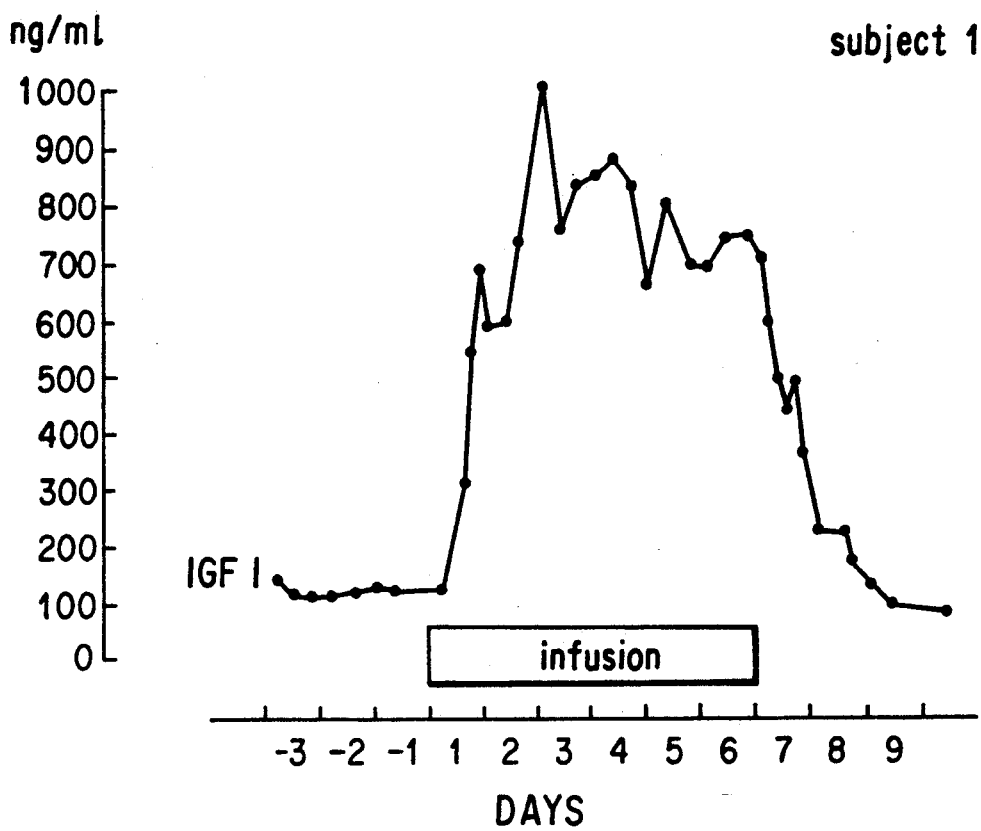
Figure 2B:
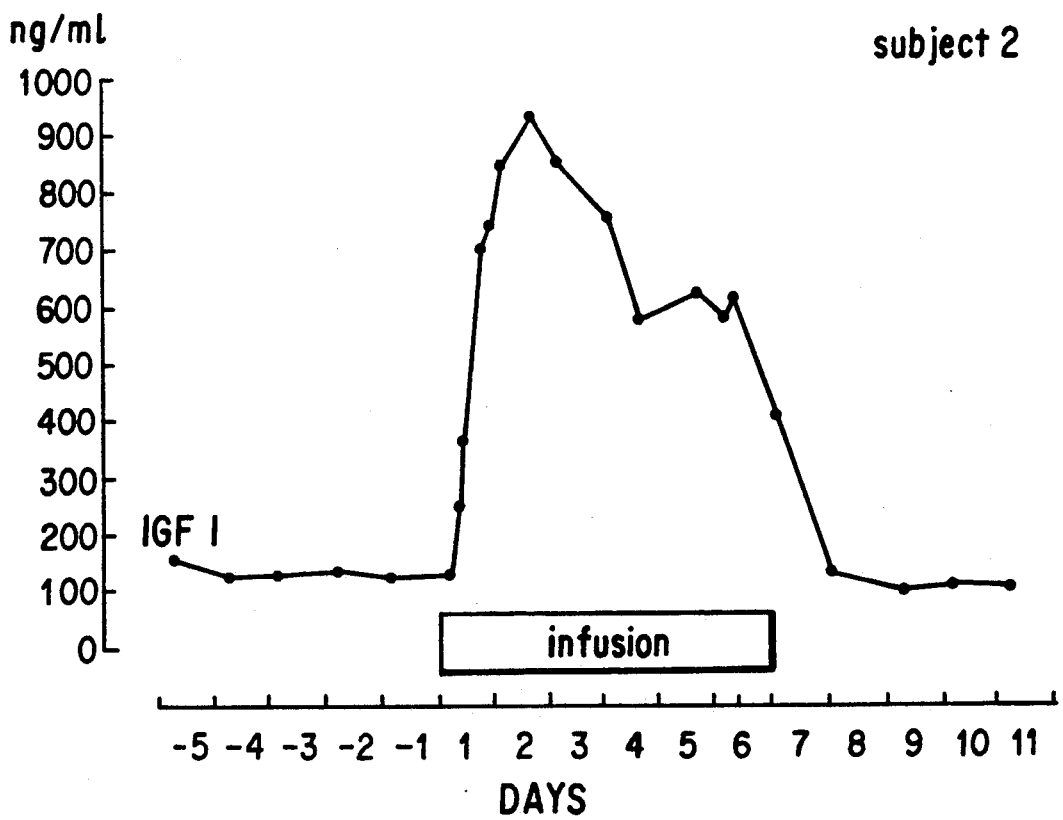

Serum Levels of Total IGF I (FIG. 2a–b)

Within hours after starting the infusion, IGF I levels rose and reached levels of 700 ng per milliliter after 13 to 14 hours. Peak levels in the two subjects were 980 and 920 ng per milliliter, respectively. When the infusion was stopped IGF I levels fell to baseline within one day.

Serum Levels of Free IGF I

Free IGF I levels during the control days were between 15 and 20 ng per milliliter and between 50 and 80 ng per milliliter during continuous IGF I infusion (7).

Figure 3A:
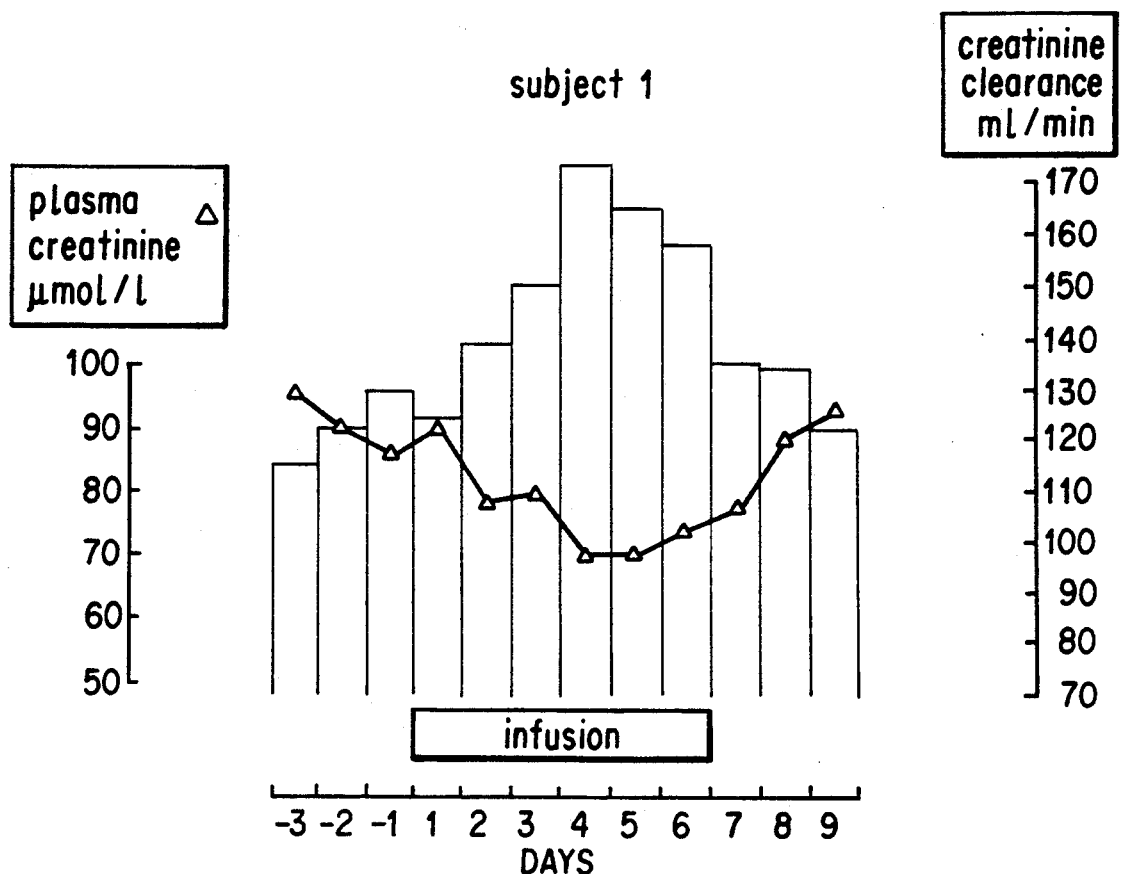
Figure 3B:
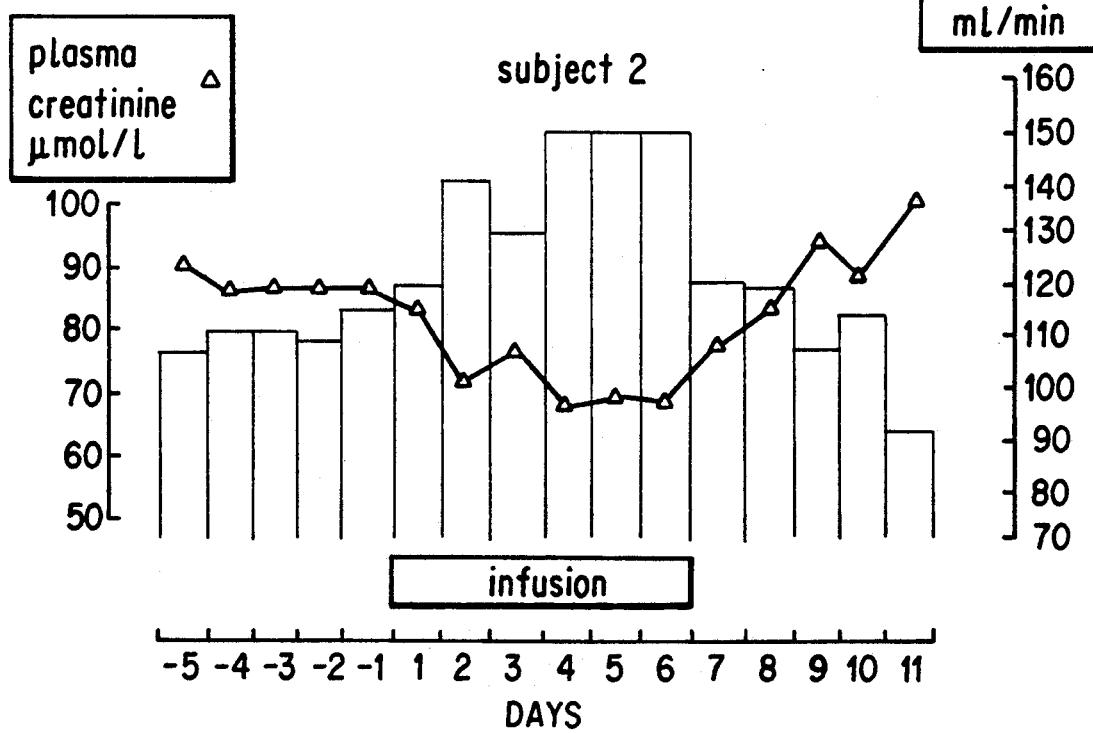

Plasma Levels of Creatinine and Creatinine Clearance (FIG. 3a–b)

Initially, the two subjects had a plasma creatinine level of 90 and 87 μmol per liter, respectively and creatinine clearances were 122 and 111 ml per minute, respectively. From days two through six of the IGF I infusion plasma creatinine was reduced to 73 μmol per liter in both subjects (corresponding to 81% and 84% of the baseline values) and creatinine clearance rose to 157 and 144 ml per minute (corresponding to 129% and 130% of control). These changes of renal function returned to preinfusion levels shortly after the infusion was stopped. Creatinine excretion per 24 hours remained constant throughout the infusion (15.8±1.1 and 14.2±1.3 mmol in subject 1 and 2, respectively).

Figure 4A:
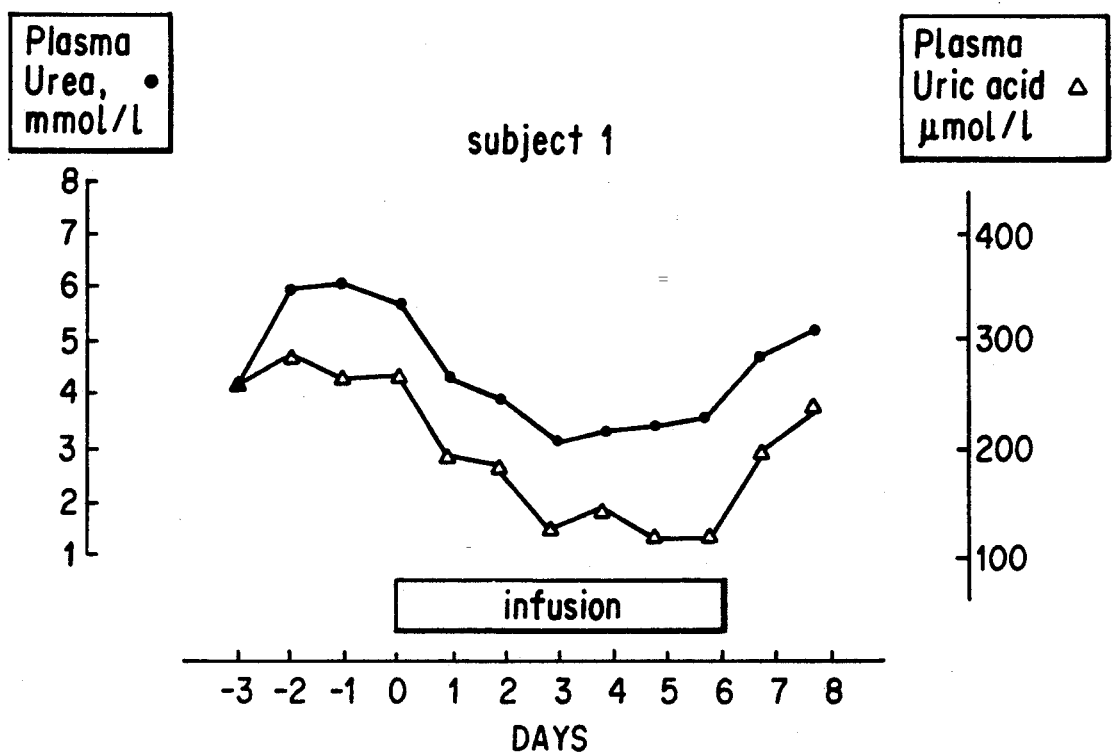
Figure 4B:
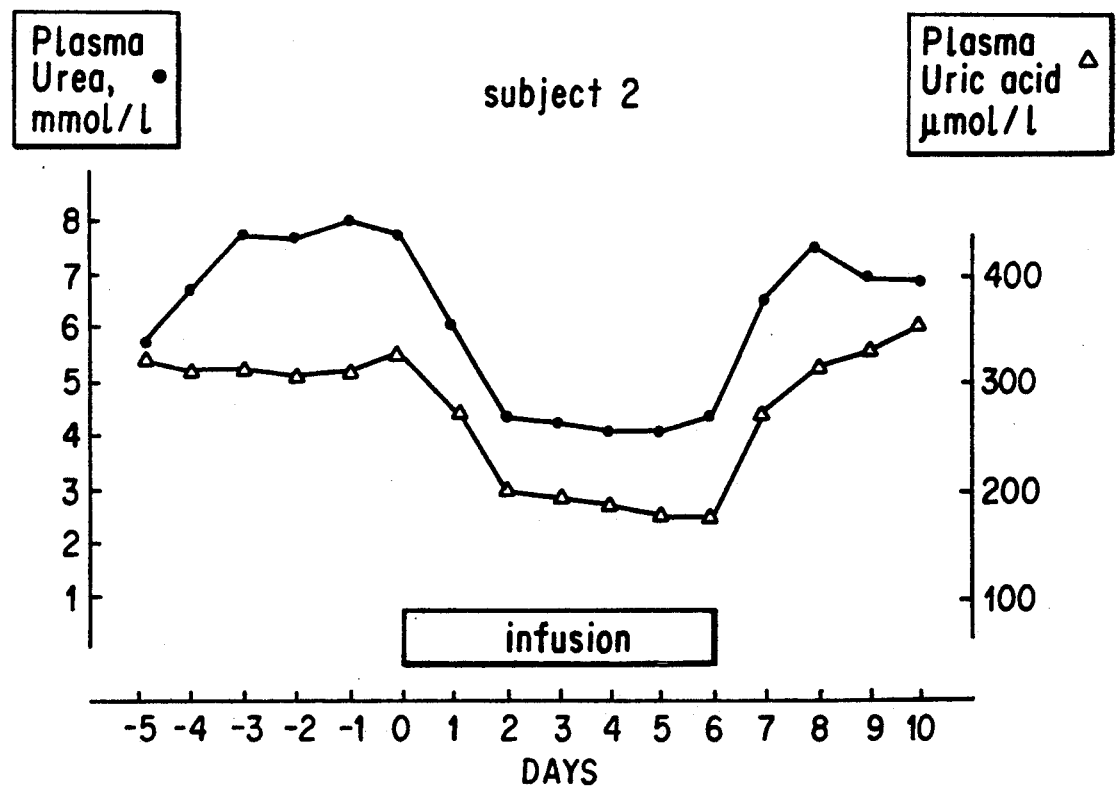

Plasma Levels of Urea and Uric Acid (FIG. 4a–b)

Plasma urea levels were 5.8 and 7.6 mmol per liter, respectively, during the initial control period. They fell to 3.4 and 4.2 mmol per liter (corresponding to 59 and 55% of baseline) within two days and remained at these levels until the infusion was stopped. Urinary excretion of urea per 24 hours was constant before, during and after the infusion (4.59±0.41 and 4.76±0.61 mmol, respectively). Plasma levels of uric acid decreased from 268 and 311 to 137 and 180 μmol per liter (51 and 58% of baseline), respectively.

2. Example for Treatment of Humans

Subjects

Two males (subject 1: 39 years, 74 kg, subject 2: 28 years, 66 kg) served as healthy subjects in this trial. They had no clinical signs and symptoms of illness and did not take any medication. Routine laboratory tests (blood, serum, urine) were within normal limits. IGF I was infused during a total of 79 hours in a dose of 20 μg/kg/hour. The subjects were on a 2000 kcal/day diet throughout the study which contained 20% protein (100 g/24 hours), 30% fat and 50% carbohydrates. Sodium chloride intake was 8 g/day. In order to prevent the thyroid gland from being filled with radioactive iodine, unlabelled sodium iodine in a dose of 10 mg p.o. per 24 hours was administered. In the same subjects similar experiments but without infusion of IGF I were performed in the weeks before and after the IGF I treatment.

Lyophilized IGF I was dissolved in 0.1 m acetic acid and infused subcutaneously at a rate of 26 μl/hour by an MRS-3-infusor (Disetronic AG, Burgdorf, Switzerland). Morning blood samples and 24 hours urine collections were obtained daily. Glomerular filtration rate (GFR) and Renal plasma flow (RPF) were measured simultaneously after overnight fasting during the hours 72 through 74. Lithium clearance was determined during the hours 72 through 79; then the infusion was stopped.

Determination of GFR and RPF: At 7 a.m. forced diuresis (10–15 ml/min) was induced by progressive p.o. water loading during 80 min. After an initial intravenous bolus of each of the isotopes, a continuous i.v. infusion of both isotopes was given. A total of 57 μCi of $^{125}$I-iodothalamate (IM.48P, Amersham, Buckinghamshire, England) and 63 μCi of $^{131}$I-iodohippurate (IB.315P, Amersham, Buckinghamshire, England) were administered during 2 hours (8,9). Urine and serum samples were collected during six intervals of 20 min. The radioactivity in serum and urine was counted in portions of 1 ml in a MR252-gamma counter (Kontron, Zürich); the values of the last five 20 min observation periods were used for the calculations. Statistical analysis was made by Student's t-test.

Lithium clearance: In order to determine the proximal and distal tubular reabsorption of fluid and sodium, the renal clearance of lithium was determined. Lithium is completely reabsorbed in the proximal tubulus whereas it is not reabsorbed at all in the distal tubulus (10). At 10 p.m. on the day before the renal function studies the subjects took 24 mmoles of lithium-sulfate (2 tablets of Lithiofor ®, Vifor SA, Geneva). Urine was collected from the time of the bolus injection of the isotopes until 7 hours later. Lithium was determined in the serum at the beginning and at the end of the collection period; the mean of both values was used for calculations. Calculations were made according to the formulas given in Table 1.

Assays

IGF I was determined by radioimmunoassay as described earlier (6). Albumin in urine was measured using an immunoturbidimetric method (commercially available kit manufactured by Miles Italiana S.p.A., Scientific Dept., Cavenago Brianza [Milan], Italy). Lithium measurements in urine and serum were performed by a Varian AA-875 atomic absorber (courtesy of the Department of Clinical Chemistry of the University Hospital of Zürich).

Results

Figure 5:
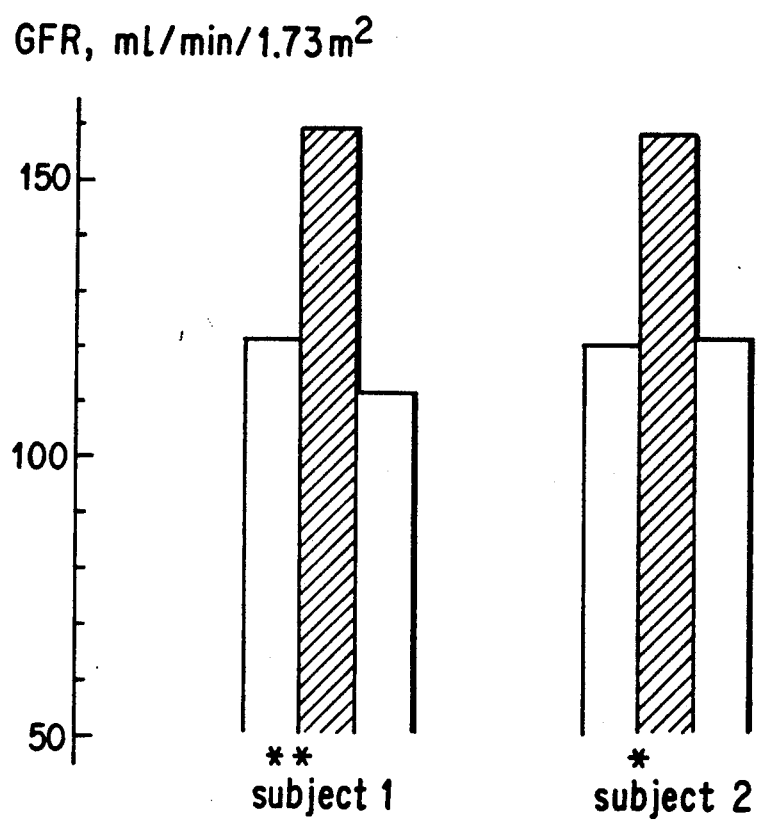
Figure 6:
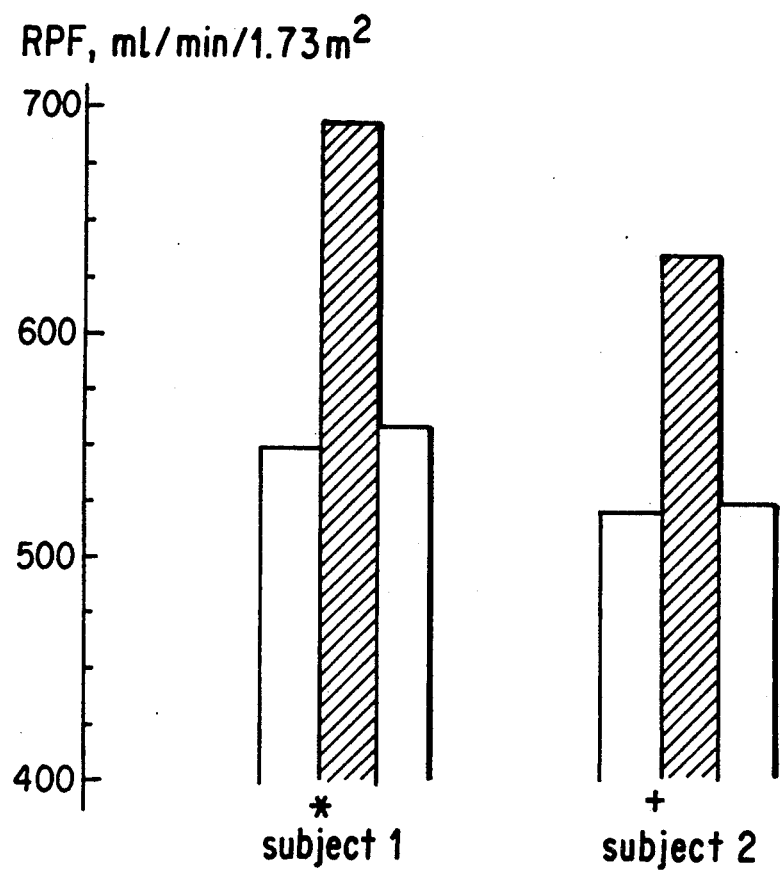

Initially, endogenous serum levels of IGF I were between 93 and 177 ng/ml. When renal function studies were performed, IGF I serum levels were 502 and 616 ng/ml in subject 1 and 2, respectively. GFR increased from 121±12 to 159±12 ml/min/1.73 m$^2$ (p<0.0005) in subject 1. Respective values in subject 2 were 120±13 and 158±16 ml/min/1.73 m$^2$ (p<0.005) (FIG. 5). Concomitantly, RPF increased from 548±56 to 692±65 ml/min/1.73 m$^2$ (p<0.005) in subject 1 and from 518±64 to 634±72 ml/min/1.73 m² (p<0.025) in subject 2, respectively (FIG. 6). A similar increase was noted in proximal and distal tubular reabsorption of fluid and sodium as calculated from lithium clearance (Table 1). All parameters had returned to baseline one week later.

Excretion of albumin in all urine samples before, during and after the infusion was less than 30 mg/24 hours; the upper limit of normal is presently assumed to be 30 mg/24 hours (11).

Body weight was constant during the infusion (74 kg in subject 1 and 66 kg in subject 2). Blood pressure, pulse rate and body temperature were within normal limits and did not change during the infusion.

In Tables 1, 2 and 3 the values for lithium clearance, creatinine clearance, osmotic and free water clearance as well as some serum parameters are given.

TABLE 1

Proximal and distal tubular reabsorption of fluid and sodium as determined by lithium clearance before (b), during [when the infusion had lasted 72 hours] (d) and after (a) constant s.c. infusion of IGF I in two healthy subjects.

|  | subject 1 | | | subject 2 | | |
| --- | --- | --- | --- | --- | --- | --- |
|  | b | d | a | b | d | a |
| prox. fluid reabsorption [GFR − $C_{Li}$; ml/min] | 87 | 112 | 87 | 93 | 114 | 95 |
| dist. fluid reabsorption [$C_{Li}$ − $V_U$; ml/min] | 29 | 41 | 18 | 20 | 38 | 20 |
| prox. Na reabsorption [(GFR − $C_{Li}$) × $P_{Na}$; mmol/min] | 12 | 16 | 12 | 13 | 16 | 11 |
| dist. Na reabsorption [($C_{Li}$ − $C_{Na}$) × $P_{Na}$; mmol/min] | 4 | 6 | 3 | 3 | 6 | 3 |

TABLE 2

Clearance calculations before (b), during (d) [when the infusion had lasted for 72 hours] and after (a) constant s.c. infusion of IGF I in two healthy subjects.

|  | subject 1 | | | subject 2 | | |
| --- | --- | --- | --- | --- | --- | --- |
|  | b | d | a | b | d | a |
| creatinine clearance; ml/min | 111 | 140 | 126 | 114 | 144 | 120 |
| osmol. clearance; ml/min [$C_{osm} = U_{osm}$: $P_{osm}$ × V] | 2.78 | 2.67 | 3.31 | 2.97 | 2.32 | 2.32 |
| free water clearance; ml/min [$C_{free\ water} = V_u − C_{osm}$] | 2.60 | 3.57 | 2.84 | 2.98 | 4.16 | 2.71 |

GFR: glomerular filtraton rate
$C_{Li}$: Li-clearance
$V_u$: urine volume/min
$P_{Na}$: plasma concentration of Na
$C_{Na}$: Na-clearance
$C_{osm}$: osmolare clearance
$U_{osm}$: urine osmolarity
$P_{osm}$: plasma osmolarity
$C_{freewater}$: free water clearance

TABLE 3

Serum parameters before (b), during (d) [when the infusion had lasted for 72 hours] and after (a) constant s.c. infusion of IGF I in two healthy subjects.

|  | subject 1 | | | subject 2 | | |
| --- | --- | --- | --- | --- | --- | --- |
|  | b | d | a | b | d | a |
| Sodium [mmol/l] | 138 | 140 | 138 | 138 | 139 | 136 |
| Potassium [mmol/l] | 4.1 | 4.2 | 4.3 | 4.8 | 4.9 | 4.8 |
| Phosphate [mmol/l] | 1.21 | 1.06 | 1.28 | 0.88 | 0.73 | 0.95 |

TABLE 3-continued

Serum parameters before (b), during (d) [when the infusion had lasted for 72 hours] and after (a) constant s.c. infusion of IGF I in two healthy subjects.

|  | subject 1 | | | subject 2 | | |
| --- | --- | --- | --- | --- | --- | --- |
|  | b | d | a | b | d | a |
| Urea [mmol/l] | 5.2 | 2.8 | 5.2 | 4.2 | 2.9 | 4.2 |
| Creatinine [umol/l] | 102 | 86 | 100 | 96 | 84 | 90 |

In a similar manner as the healthy subjects patients with renal diseases can be treated.

3. Example for Treatment of Mini-Poodles

Animals

All mini-poodles were purchased from one breeder. They were offsprings of one male (34 cm shoulder height) and two females (30 and 32 cm shoulder height). At the age of 60 days they were transferred to our animal care facility. One litter was used for the IGF I infusion and another litter served as control. Animals from one litter were housed together from birth to the end of the experiment at the age of 221 when radial epiphyseal plates were ossified. The dogs had free access to water and received standard protein rich dog food ad libitum twice daily. They were weighed daily between 7 and 9 a.m.. The left forelegs were X-rayed every other week by the same two persons using the same X-ray device. The length of the radius was measured on the film. Blood was drawn by venipuncture on the foreleg every other week.

Subcutaneous infusion of IGF I

Four mini-poodles (two males and two females) received subcutaneous infusions of IGF I from day 91 to 221 of age, i.e. during a total of 130 days. MRS 3-Infusors ® (manufactured by Disetronic AG, Burgdorf,, Switzerland) were fixed on the neck of the dogs in a specially designed garmet which covered and protected the subcutaneous catheter (Abbocath-T ®, 24 G × 19 mm, Abbot Ireland Ltd). The catheter was fixed by adhesive tape to the shaved skin of the dog and changed every fourth day. The peptide was dissolved in 0.1M acetic acid and infused at a rate of 24 to 26 μl/hour/day. The dose of IGF I was kept constant at 6 mg/day per poodle. Per kg b.w. the dose of IGF I was 2 mg initially and decreased to around 1 mg at the end of the infusion period. Correct function of the infusion system was checked every 12 hours. Four control mini-poodles (one male, three females) were kept and handled in the same way as the IGF I infused animals, except that their garmet did not contain the infusor. No adverse signs or symptoms and no changes in routine hematological and blood-chemical assays were observed during the whole IGF I infusion period.

Assays

Radioimmunoassay for IGF I: This assay was performed after removal of the binding proteins by SEP-PAK $C_{18}$ cartridges (Waters Associates, Milford MA). Polyclonal rabbit antibodies against a human IGF I crossreacting with dog IGF I were used and human IGF I served as standard (6). Mean IGF I levels were three times higher in the IGF I infused animals than in the controls.

Serum levels of creatinine

Figure 7:
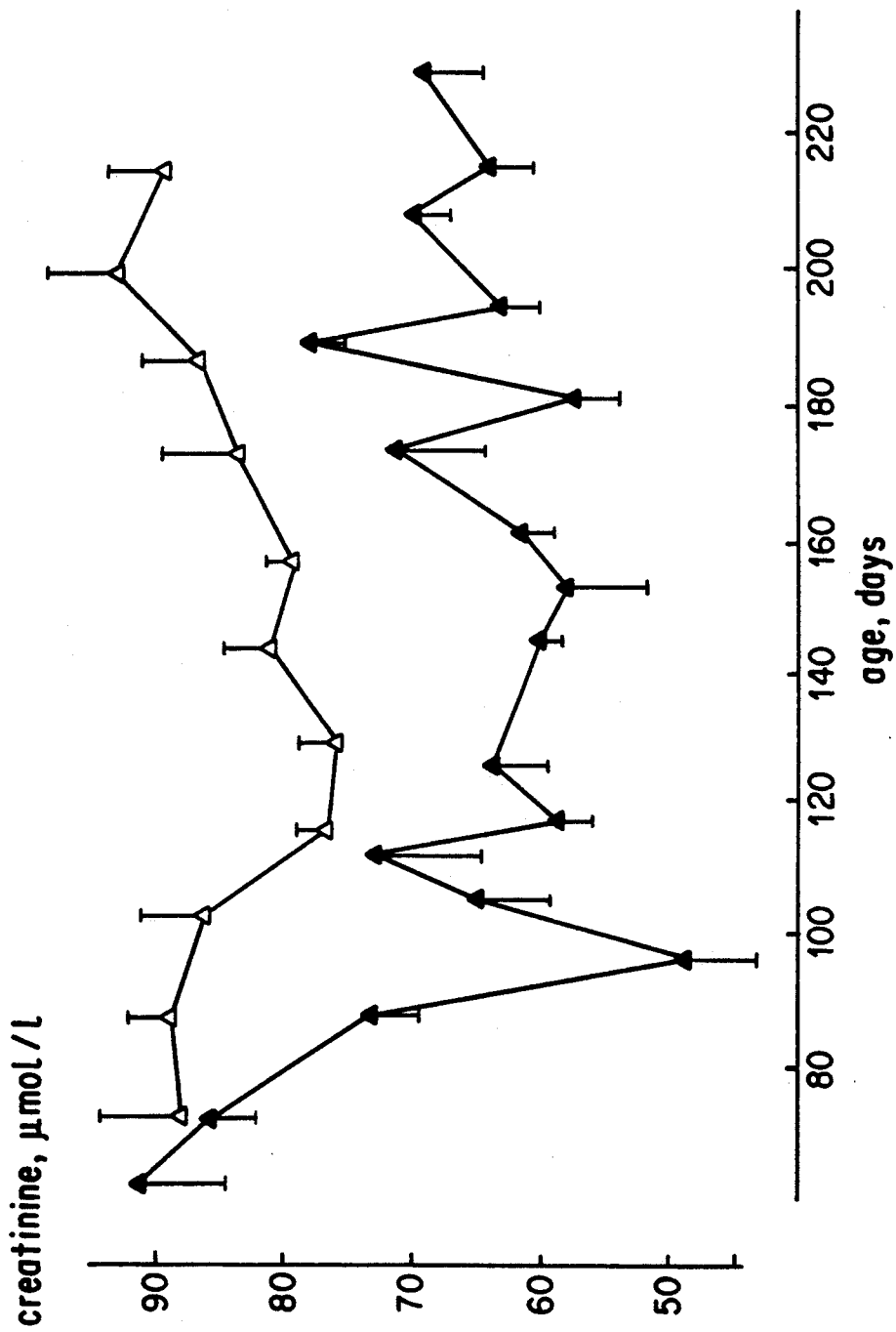

Mean serum levels of creatinine were significantly lower during the entire IGF I infusion period than in the control group (FIG. 7).

LEGEND TO FIGURES

FIG. 1: Blood glucose and free IGF I serum levels on the first day of continuous s.c. infusion of recombinant IGF I at a rate of 32.0 μg per kilogram body weight and hour in subject 1. The infusion was begun at 6.30 a.m. and stopped at 8.00 p.m. when blood glucose had fallen to 2.6 mmol per liter. Serum levels of free IGF I by that time had increased from basel values of 20 ng per milliliter to 123 ng per milliliter. "M" indicates the time of the meals.

FIG. 2: Serum levels of total IGF I in two subjects before, during and after six days under constant s.c. infusion of recombinant IGF I in a dose of 20.0 μg per kilogram body weight and hour.

FIG. 3: Plasma levels of creatinine (Δ) and creatinine clearance (represented by bars) in two subjects before, during and after six days under constant s.c. infusion of recombinant IGF I in a dose of 20.0 μg per kilogram body weight and hour.

FIG. 4: Plasma levels of urea and uric acid in two subjects during constant s.c. infusion of recombinant IGF I in a dose of 20.0 μg per kilogram body weight and hour.

FIG. 5: Glomerular Filtration Rate (GFR) as determine by $^{125}$I-iodothalamate clearance before, during and after constant s.c. infusion of IGF I in two healthy subjects. Mean values of five 20 min-observation periods are represented. Numeric means±SD are given in the result section.

FIG. 6: Renal Plasma Flow (RPF) as determined by $^{125}$I-iodohippurate clearance before, during and after constant s.c. infusion of IGF I in two healthy subjects. Mean values of five 20 min-observation periods are represented. Numeric means±SD are given in the result section.

FIG. 7: Serum levels of creatinine in four mini-poodles infused with IGF I (▲) and in four controls (Δ). Mean ±SEM.

REFERENCES

1. Guler HP, Zapf J, Froesch ER. Short-term metabolic effects of recombinant human insulin-like growth factor I in healthy adults. N Engl J Med 1987; 317:137-40.
2. Guler HP, Zenobi P, Zapf J, et al. IGF I and II and recombinant human IGF I are hypoglycemic in the rat, mini-pig, and men. Endocrinology 1986; 118: Suppl:129, abstract.
3. Scheiwiller E, Guler HP, Merryweather J, Scandella C, Maerki W, Zapf J, Froesch ER. Growth restoration of insulin-deficient diabetic rats by recombinant human insulin-like growth factor I. Nature 1986; 323:169-71.
4. van Buul-Offers S, Ueda I, Van den Brandle JL. Biosynthetic somatomedin C (SM-C/IGF-I) increases the length and weight of Snell dwarf mice. Pediatr Res 1986; 20:825-7.
5. Guler HP, Zapf J, Froesch ER. S.c. infusion of recombinant human insulin-like growth factor I (rhIGF I) stimulates growth of hypophysectomized rats continuously during 18 days. Proceedings of the 1st European Congress of Endocrinology, Copenhagen 1987; 103, abstract 12-390.
6. Zapf J, Walter H, Froesch ER. Radioimmunological determination of insulin-like growth factors I and II in normal subjects and in patients with growth disorders and extrapancreatic tumor hypoglycemia. J Clin Invest 1981; 68:1321-30.
7. Zapf J, Hauri C, Waldvogel M, Froesch ER. Acute metabolic effects and half-lives of intravenously administered insulin-like growth factors I and II in normal and hypophysectomized rats. J. Clin Invest 1986; 77:1768-75.
8. MOGENSEN CE: Glomerular filtration rate and renal plasma flow in short-term and long-term juvenile diabetes mellitus. Scand J Clin Lab Invest 28:91-100, 1971.
9. MARRE M, LEBLANC H, SUAREZ L, GUYENNE TT, MENARD J, PASSA P: Converting enzyme inhibition and kidney function in normotensive diabetic patients with persistent microalbuminuria. Br Med J 294:1448-1452, 1987.
10. THOMSEN K: Lithium clearance: A new method for determining proximal and distal tubular reabsorption of sodium and water. Nephron 37:217-223, 1984.
11. JENSEN T, RICHTER EA, FELDT-RASMUSSEN B, KELLBAEK H, DECKERT T: Impaired aerobic work capacity in insulin dependent diabetics with increased urinary albumin excretion. Br Med J 296:1352-1410, 1988.

We claim:

1. A method for the treatment of patients suffering from a renal disease selected from the group consisting of glomerulitis, interstitial nephritis, pyelonephritis, glomerulosclerosis, Kimmelstiel-Wilson in diabetic patients, chronic kidney failure and kidney failure after kidney transplantation, said method comprising administering an effective amount of IGF I to said patients.

2. A method for the treatment of patients suffering from a renal disease selected from the group consisting of glomerulitis, interstitial nephritis, pyelonephritis, glomerulosclerosis, Kimmelstiel-Wilson in diabetic patients, chronic kidney failure and kidney failure after kidney transplantation according to claim 1, wherein the administration of IGF I improves glomerular filtration and renal plasma flow.

3. A method according to claim 1, wherein the IGF I administered is, recombinant human IGF I.

4. A method according to claim 1, wherein IGF I is administered in an amount of from about 24 ug/kg/day up to about 720 ug/kg/day.

5. A method according to claim 1, wherein IGF I is subcutaneously or intravenously infused via a minipump.

6. A method according to claim 1, wherein IGF I is subcutaneously, intravenously or intramuscularly administered continuously in a dose of about 1 ug/kg/h up to about 30 ug/kg/h.

* * * * *